United States Patent [19]

Asakura et al.

[11] Patent Number: 5,093,127
[45] Date of Patent: Mar. 3, 1992

[54] PREPARATION OF FR115224 SUBSTRATE FOR PARENTERAL ADMINISTRATION

[75] Inventors: Sotoo Asakura, Kyoto; Nobuto Kanagawa, Toyonaka; Kiyota Youhei, Ikeda, all of Japan

[73] Assignee: Fujisawa Pharmaceutical Co., Ltd., Osaka, Japan

[21] Appl. No.: 525,025

[22] Filed: May 18, 1990

[30] Foreign Application Priority Data

Jun. 2, 1989 [JP] Japan .................. 1-141972

[51] Int. Cl.⁵ .................. A61K 37/02; C07K 7/64; C08B 37/16
[52] U.S. Cl. .................. 424/434; 424/422; 424/427; 424/428; 424/430; 424/433; 424/435; 424/436; 424/437; 514/9; 514/54; 514/58; 514/60; 514/885; 514/953; 514/954; 514/955; 514/969; 530/317; 530/812; 530/813; 536/45; 536/46
[58] Field of Search ............... 424/422, 427, 428, 430, 424/433, 434, 435, 436, 437; 514/9, 54, 58, 60, 885, 953, 954, 955, 955, 969; 530/317, 812-815; 536/45, 46

[56] References Cited

U.S. PATENT DOCUMENTS 4,933,323  6/1990  Noguchi et al. .................. 530/330

FOREIGN PATENT DOCUMENTS 336230  10/1989  European Pat. Off. .
2226023  6/1990  United Kingdom .
8808304  11/1988  World Int. Prop. O. .

Primary Examiner—Thurman K. Page
Assistant Examiner—Carlos Azpuru
Attorney, Agent, or Firm—Oblon, Spivak, McClelland, Maier & Neustadt

[57] ABSTRACT

A cyclic peptide designated FR115224, administered parenterally in a cyclodextrin carrier, which exhibits antiallergic activity.

4 Claims, No Drawings

PREPARATION OF FR115224 SUBSTRATE FOR PARENTERAL ADMINISTRATION

BACKGROUND OF THE INVENTION

1. Field of the Invention

The present invention relates to cyclodextrin-containing preparations for parenteral administration and more particularly, to preparations containing FR115224 substance and cyclodextrin for parenteral administration. The preparations are utilized in the medical field.

2. Statement of the Prior Art

It is known that cyclodextrin forms a so-called inclusion compound in which a drug molecule is enclosed, to enhance solubility of a sparingly water-soluble drug.

As an example, it is reported that Cinnarizine which is a sparingly water-soluble cerebro-vasodilator forms an inclusion compound with β-cyclodextrin, whereby its water solubility at 20° C. can be increased by about 5 times [Chemical & Pharmaceutical Bulletin, 32 (10), 4179–4184 (1984)].

FR115224 substance shown by the following chemical structure:

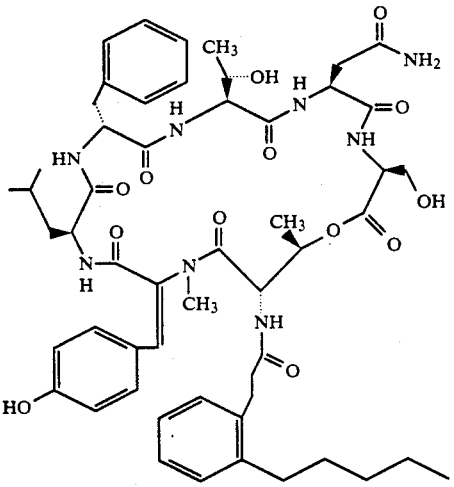

is a cyclic peptide compound having a molecular weight of 1041 and has an antiallergic activity.

This FR115224 substance has a large molecular weight so that it is absorbed through the digestive organ only with difficulty, when it is orally administered.

Therefore, parenteral administration such as perocular or pernasal administration or inhalation, etc. is conceivable but due to poor solubility in water, FR115224 substance is inferior in its absorbability and thus involves a problem that a sufficient pharmaceutical effect cannot be expected.

SUMMARY OF THE INVENTION

In order to improve the solubility of FR115224 substance in water, the present inventors have made investigations on various solubilizing agents and as a result, have found that when cyclodextrin is used as a solubilizing agent, the solubility of FR115224 substance in water can be markedly increased, in spite that FR115224 substance forms no inclusion compound with cyclodextrin because morecular weight of FR115224 substance is large.

In addition, a preparation comprising FR115224 substance and cyclodextrin for parenteral administration was prepared and administered in vivo. It has been found that the absorbability of FR115224 substance in the preparation can be markedly improved as compared to a parenteral administration in which no cyclodextrin is formulated. The present invention has thus been accomplished.

As the preparation for parenteral administration of the present invention, there are preparations suited for antiallergic agents, for example, an eye drop, a nose drop, an injection, inhalation composition (e.g., aerosol, powdery inhalation composition, liquid inhalation composition, etc.), an ointment, a cream, etc.

Example of cyclodextrin which can be used in the present invention include α-cyclodextrin, β-cyclodextrin, hydroxypropyl β-cyclodextrin, γ-cyclodextrin, dimethyl-β-cyclodextrin, etc. Of these, β-cyclodextrin and hydroxypropyl β-cyclodextrin are particularly preferred since the solubility of FR115224 substance in water ca increase especially greatly.

The cyclodextrin content in the parenteral preparation of the present invention is not particularly limited but an amount of 0.5 to 20 times the content of FR115224 substance contained in the preparation sufficiently exhibits its solubilizing effect.

Next, a process for producing the parenteral preparation of the present invention is described below.

For preparing aqueous preparations such as an eye drop, a nose drop, injection, etc., FR115224 substance is added to purified water or distilled water for injection and cyclodextrin is added to the mixture. The mixture was stirred to dissolve FR115224 substance.

If necessary and desired, additives conventionally used, such as an isotonic agent (for example, sodium chloride, etc.), a buffering agent (for example, boric acid, sodium monohydrogenphosphate, sodium dihydrogenphosphate, etc.), a preservative (for example, benzalkonium chloride, etc.), a thickener (for example, carboxyvinyl polymer, etc.) may also be added to these preparations.

For preparing aerosol, FR115224 substance and cyclodextrin are finely ground preferably into 5 μm or less, respectively, in a conventional manner; if necessary and desired, a dispersing agent is added to the powders and the mixture is packed in a spray container under cooling, together with a propellant to prepare aerosol. In this case, FR115224 substance and cyclodextrin may be dissolved in a mixture of an organic solvent (for example, ethanol, etc.) and water. The solvent is evaporated by heating under reduced pressure and the resulting mixture of FR115224 substance and cyclodextrin may also be finely divided for use.

As preferred examples of the dispersing agent, there are nonionic surface active agents which are commercially available under the trademarks of Span 80, Span 85, etc., amphoteric surface active agents such as soybean lecithin, etc.; natural alcohols such as oleyl alcohol, etc.

As preferred examples of the propellant, there are CFC(chlorofluorocarbon) 11, CFC 12, CFC 114 which are fluorochlorinated lower alkanes, and a mixture thereof.

In the inhalation composition, liquid inhalation composition can be prepared in a manner similar to the case of preparing aqueous preparations such as an eye drop, etc. described above. Additives similar to those described above are added to the inhalation composition, if necessary and desired. The liquid inhalation composition is administered using an equipment for inhalation such as Nebuliser (trademark), etc.

The powdery inhalation composition can be prepared by mixing, if necessary and desired, an excipient such as lactose, etc., with the fine powder mixture or the respective fine powders of FR115224 substance and cyclodextrin prepared in a manner similar to the aerosol composition described above. The powdery inhalation composition is administered using an equipment for inhalation such as Spinhaler (trademark), etc.

The ointment and cream is prepared by adding FR115224 substance and cyclodextrin to a base (for example, white vaseline, liquid paraffin, etc.) melted by heating and, if necessary and desired, mixing conventional additives such as a preservative, an antioxidant, a stabilizer, a moisturizer, a pH controlling agent, etc., with the mixture.

The effects of the present invention are explained by referring to the following test examples.

Solubility test

Method

FR115224 substance (125 mg) was charged in 13 sample bottles, respectively and distilled water (2.5 ml) was added thereto.

Then, $\alpha$-cyclodextrin, $\beta$-cyclodextrin, hydroxypropyl $\beta$-cyclodextrin or $\gamma$-cyclodextrin was charged to each of the sample bottles in amounts of 0.4 mg (cyclodextrin content: 0.16% w/v), 2.5 mg (cyclodextrin content: 1% w/v) or 12.5 mg (cyclodextrin content: 5% w/v), respectively. No cyclodextrin was charged in one sample bottle, which was made control. After stirring at room temperature for 12 hours, the concentration of FR115224 substance in each aqueous phase was measured to determine the solubility of FR115224 substance.

The results are shown in Table 1.

Results

TABLE 1

| Solubility of FR115224 substance (% w/v) | | | | |
|---|---|---|---|---|
| | Addition amount of cyclodextrin (% w/v) | | | |
| | 0 | 0.16 | 1 | 5 |
| $\alpha$-Cyclodextrin | 0.003 | 0.008 | 0.03 | 0.14 |
| $\beta$-Cyclodextrin | 0.003 | 0.013 | 0.11 | 0.34 |
| Hydroxypropyl $\beta$-Cyclodextrin | 0.003 | 0.009 | 0.06 | 0.49 |
| $\gamma$-Cyclodextrin | 0.003 | 0.006 | 0.03 | 0.16 |

From the results, it is noted that cyclodextrin can markedly increase the solubility of FR115224 substance in water.

Bioavailability test

Method

SD strain male rats (weighing 250 to 300 g) of 7 to 8 week old were fixed at the back. After ethereal anesthesia, the fore neck was incised to expose the trachea. Then, a hole was formed between the thyroid cartilage rings of the rat trachea.

A spray nozzle was mounted to the aerosol composition obtained in Examples 1 and 2 and Reference Example 1 described hereinafter. After one empty injection, the nozzle was inserted into the trachea at a depth of 5 to 7 mm and FR115224 substance was propelled in a dose of 5 mg/kg rat body weight. Blood was collected from the heart 0.25, 0.5, 1, 2, 4, 6 and 24 after administration. Plasma was fractionated by centrifugation and the concentration of FR115224 substance in plasma was measured by high performance liquid chromatography.

AUC (area under plasma concentration-time curve) between 0 and 24 hours was determined by the trapezoid method.

The results are shown in Table 2.

Results

TABLE 2

| | Concentration of FR115224 substance in plasma ($\mu$g/ml) | | | | | | | AUC 0-24 hrs. ($\mu$g · hr · ml$^{-1}$) |
|---|---|---|---|---|---|---|---|---|
| Preparation | 0.25 hr. | 0.5 hr. | 1 hr. | 2 hrs. | 4 hrs. | 6 hrs. | 24 hrs. | |
| Example 1 | 0.147 | 0.237 | 0.428 | 0.144 | 0.335 | 0.313 | 0.160 | 6.43 |
| Example 2 | 0.165 | 0.136 | 0.079 | 0.128 | 0.115 | 0.094 | 0.057 | 2.15 |
| Reference Example 1 | 0.023 | 0.026 | 0.051 | 0.027 | 0.042 | 0.023 | 0 | 0.32 |

(shown by a mean value of 3 in each case)

The test results reveal that the aerosol composition of the present invention provides markedly excellent absorption of FR115224 substance in the lung, as compared to the aerosol composition of Reference Example 1 in which no cyclodextrin was added.

REFERENCE EXAMPLE 1

After FR115224 substance (0.1 g) and soybean lecithin (0.2 g) were weighed in an aerosol can, CFC mixture ( CFC 12 : CFC 11 : CFC 114 = 65 : 17.5 : 17.5) cooled with a mixture of methanol and dry ice was added to the mixture. A valve was then mounted to the can. After the temperature was reverted to room temperature, the mixture was dispersed by ultrasonic wave to obtain an aerosol composition having the following composition.

| FR115224 substance | 0.1 g |
|---|---|
| Soybean lecithin | 0.2 g |
| CFC mixture | q.s. |
| | 20 ml |

EXAMPLES

Hereafter the present invention is described by referring to the examples.

EXAMPLE 1

FR115224 substance (2 g) and $\beta$-cyclodextrin (14 g) were dissolved in 50% ethanol solution (1 liter). The solvent was removed by a rotary evaporator on a water bath at 40° to 50° C. under reduced pressure. After the resulting mixture was roughly ground in a mortar in a nitrogen flow, the powders were finely ground in a particle size of 5 $\mu$m or less using a jet mill (model TJ-60). The thus obtained mixture (0.8 g) of FR115224 substance and $\beta$-cyclodextrin and soybean lecithin (0.2 g) were weighed in an aerosol can and a CFC mixture ( CFC 12 : CFC 11 : CFC 114 = 65 : 17.5 17.5) cooled with a mixture of methanol and dry ice was added to the mixture. A valve was then mounted to the can. After the temperature was reverted to room temperature, the mixture was dispersed by ultrasonic wave to obtain an aerosol composition comprising FR115224 substance and β-cyclodextrin in a ratio of 1:7, having the following composition.

| | |
|---|---|
| FR115224 substance | 0.1 g |
| β-cyclodextrin | 0.7 g |
| Soybean lecithin | 0.2 g |
| CFC mixture | q.s. |
| | 20 ml |

EXAMPLE 2

In a manner similar to Example 1, an aerosol composition comprising FR11524 substance and β-cyclodextrin in a ratio of 1:1 having the following composition was obtained.

| | |
|---|---|
| FR115224 substance | 0.1 g |
| β-cyclodextrin | 0.1 g |
| Soybean lecithin | 0.2 g |
| CFC mixture | q.s. |
| | 20 ml |

EXAMPLE 3

FR115224 substance, β-cyclodextrin, benzalkonium chloride, anhydrous sodium dihydrognphosphate, anhydrous sodium monohydrogenphosphate and sodium chloride were added to sterile purified wate. The mixture was stirred and dissolved to obtain an eye drop having the following composition.

| | |
|---|---|
| FR115224 substance | 0.2 g |
| β-cyclodextrin | 3 g |
| Benzalkonium chloride | 0.01 g |
| Anhydrous sodium dihydrogenphosphate | 0.56 g |
| Anhydrous sodium monohydrogenphosphate | 0.284 g |
| Sodium chloride | 0.31 g |
| Sterile purified water | q.s. |
| | 100 ml |

EXAMPLE 4

FR115224 substance, β-cyclodextrin, methyl p-oxybenzoate and ethyl p-oxybenzoate were added to sterile purified water. The mixture was stirred and dissolved to obtain a nose drop having the following composition.

| | |
|---|---|
| FR115224 substance | 0.2 g |
| β-cyclodextrin | 3 g |
| Methyl p-oxybenzoate | 0.02 g |
| Ethyl p-oxybenzoate | 0.01 g |
| Purified water | q.s. |
| | 100 ml |

EXAMPLE 5

FR115224 substance, β-cyclodextrin and benzalkonium chloride were added to purified water. The mixture was stirred and dissolved to obtain a liquid inhalation composition having the following composition.

| | |
|---|---|
| FR115224 substance | 0.1 g |
| β-cyclodextrin | 1.5 g |

-continued

| | |
|---|---|
| Benzalkonium chloride | 0.01 g |
| Purified water | q.s. |
| | 100 ml |

EXAMPLE 6

FR115224 substance and β-cyclodextrin are ground in a particle size of 5μm or less using a jet mill (made by Fuji Industry Co., Ltd.), respectively and then they are mixed with lactose to obtain a powdery inhalation composition having the following composition.

| | |
|---|---|
| FR115224 substance (particle size: 5 μm or less) | 6.3 mg |
| β-cyclodextrin (particle size: 5 μm or less) | 43.7 mg |
| lactose | 50 mg |
| | 100 mg |

EXAMPLE 7

FR115224 substance, α-cyclodextrin, propylene glycol and methyl p-oxybenzoate were added to purified water. The mixture was heated at 70° C. to dissolve them.

Stearyl alcohol, polyoxyethylene-hardened castor oil, glycerine monostearate and propyl p-oxybenzoate were added to white vaseline. The mixture was heated at 70° C. to dissolve.

The aqueous phase componenets and oily phase components described above were mixed and stirred with heating (70° C.) to obtain a cream composition having the following composition.

| | |
|---|---|
| FR115224 substance | 0.2 g |
| α-cyclodextrin | 3 g |
| White vaseline | 3 g |
| Stearyl alcohol | 20 g |
| Propylene glycol | 12 g |
| Polyoxyethylene-hardened castor oil | 4 g |
| Glycerine monostearate | 1 g |
| Methyl p-oxybenzoate | 0.1 g |
| Propyl p-oxybenzoate | 0.1 g |
| Purified water | q.s. |
| | 100 g |

EXAMPLE 8

FR115224 substance and α-cyclodextrin were added to propylene glycol. The mixture was heated at 70° C. to dissolve them. The resulting mixture was added to and mixed with a melt of white wax, liquid paraffin and white vaseline heated at 70° C. to obtain an ointment having the following composition.

| | |
|---|---|
| FR115224 substance | 0.2 g |
| α-cyclodextrin | 3 g |
| White wax | 7.8 g |
| Liquid paraffin | 15 g |
| White vaseline | 69 g |
| Propylene glycol | 5 g |
| | 100 g |

What we claim is:

1. A preparation for parenteral administration comprising an effective amount of FR115224 substance for those in need of its antiallergic activity, of the formula:

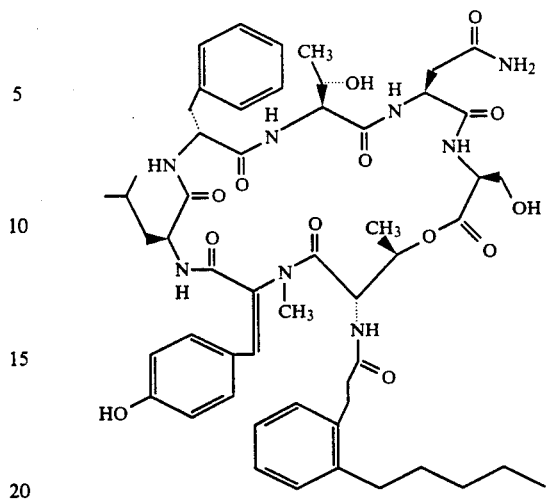

and cyclodextrin in an amount of 0.5 to 20 times the content of FR115224 substance.

2. A preparation for parenteral administration as claimed in claim 1, wherein said cyclodextrin is β-cyclodextrin.

3. A preparation for parenteral administration as claimed in claim 1 or 2, which is selected from the group consisting of an eye drop, a nose drop, an injection, an inhalation composition, an ointment and a cream.

4. A preparation for parenteral administration as claimed in claim 3, which is an inhalation composition.

* * * * *

UNITED STATES PATENT AND TRADEMARK OFFICE
CERTIFICATE OF CORRECTION

PATENT NO.  : 5,093,127
DATED       : March 3, 1992
INVENTOR(S) : Sotoo Asakura et al.

It is certified that error appears in the above-identified patent and that said Letters Patent is hereby corrected as shown below:

Title page, item [54], and col. 1, lines 1-4,
                        should read      --PREPARATION OF FR115224

SUBSTANCE FOR PARENTERAL ADMINISTRATION--

Title page, item [75], third inventor's name, should read
--Youhei Kiyota--.

Signed and Sealed this

First Day of June, 1993

Attest:

MICHAEL K. KIRK

*Attesting Officer*     Acting Commissioner of Patents and Trademarks